United States Patent [19]

Grim

[11] Patent Number: 5,232,457

[45] Date of Patent: Aug. 3, 1993

[54] MEDICAL SYRINGE

[76] Inventor: John P. Grim, 2399 Oak Ct., Orange Park, Fla. 32073

[21] Appl. No.: 740,432

[22] Filed: Aug. 5, 1991

[51] Int. Cl.⁵ ............................................. A61M 5/32
[52] U.S. Cl. .................................. 604/195; 604/197; 604/198; 604/228; 604/239
[58] Field of Search ........ 604/110, 162, 263, 194–198, 604/187, 218, 232, 192, 228, 239; 128/919

[56] References Cited

U.S. PATENT DOCUMENTS

| | | | |
|---|---|---|---|
| 2,193,322 | 3/1940 | Lozier et al. | 604/88 |
| 2,244,969 | 6/1941 | Smith | 604/91 |
| 2,705,956 | 4/1955 | McLaughlin | 604/415 |
| 3,583,399 | 6/1971 | Ritsky | 604/900 |
| 3,584,626 | 6/1971 | Johansson | 604/194 |
| 4,808,169 | 2/1989 | Haber et al. | 604/195 |
| 4,834,717 | 5/1989 | Haber et al. | 604/193 |
| 4,927,414 | 5/1990 | Kulli | 604/198 |
| 4,941,883 | 7/1990 | Venturini | 604/195 |
| 4,943,282 | 7/1990 | Page et al. | 604/198 |

Primary Examiner—C. Fred Rosenbaum
Assistant Examiner—Mark Bockelman
Attorney, Agent, or Firm—Arthur G. Yeager

[57] ABSTRACT

A medical syringe having a disposable capsule, or capsule, containing the needle and the injection fluid, the syringe including a barrel assembly having a thumb ring attached to a plunger by a plurality of connecting rods, the plunger working like a piston inside a barrel having finger grips to cooperate with the thumb ring and a central locking rod to connect to a disposable shielded needle capsule, the capsule including a space for holding the supply of injection fluid and a movable piston at the top of that space for contact with the plunger, and a central tubular guide as a sheath for a hollow needle having a needle plug which is attachable to the locking rod and two spaced gaskets around the needle and positioned on each side of a passageway through the wall to be in alignment with a passageway through the tubular guide to allow the fluid to flow into the hollow of the needle.

30 Claims, 4 Drawing Sheets

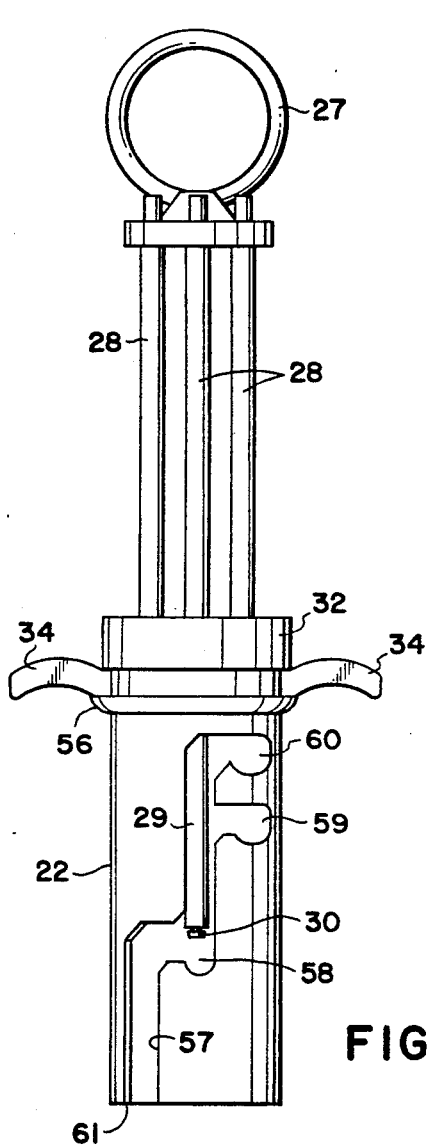
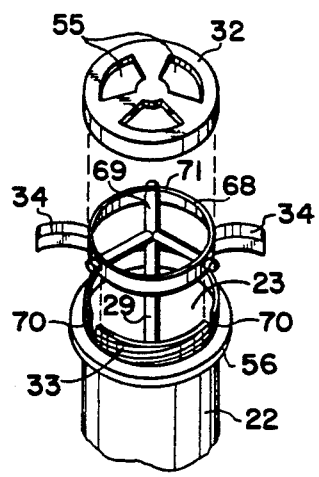
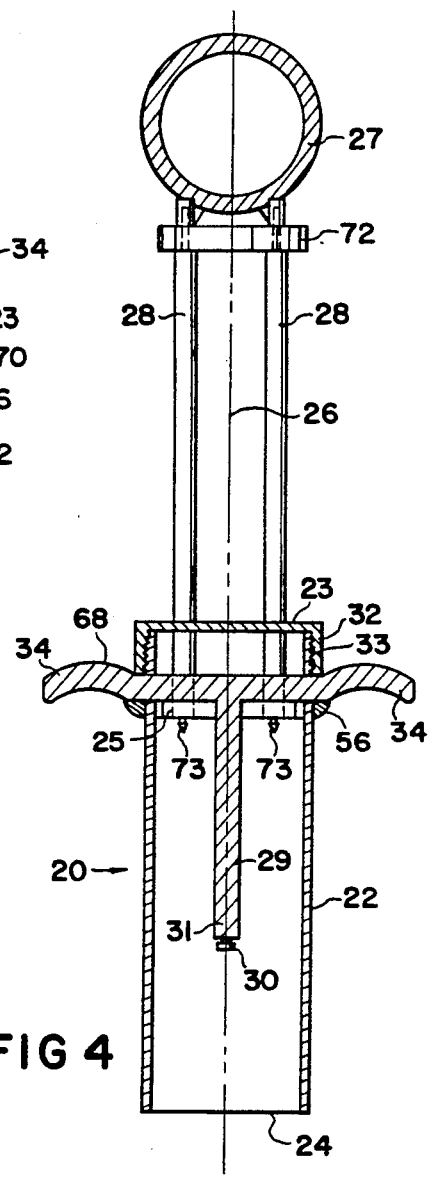
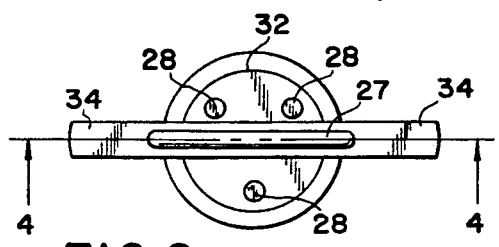
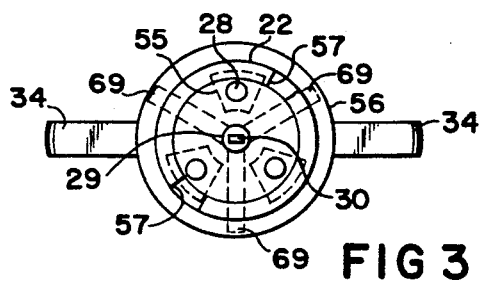

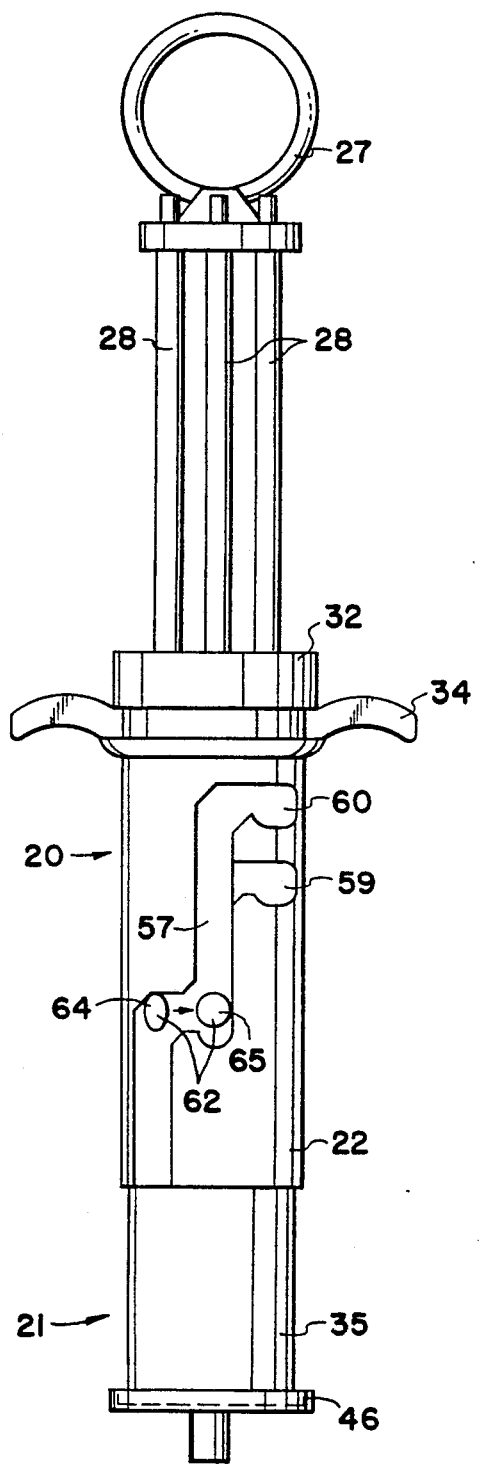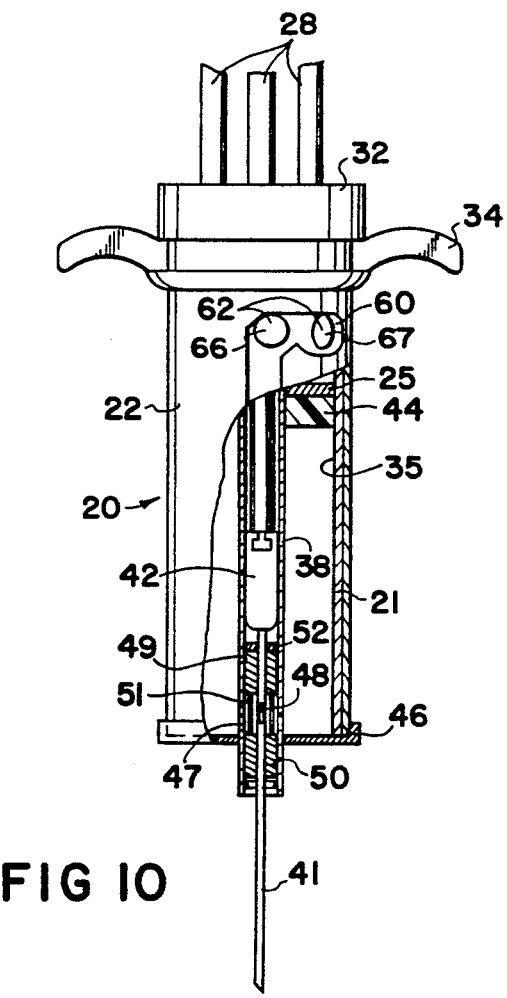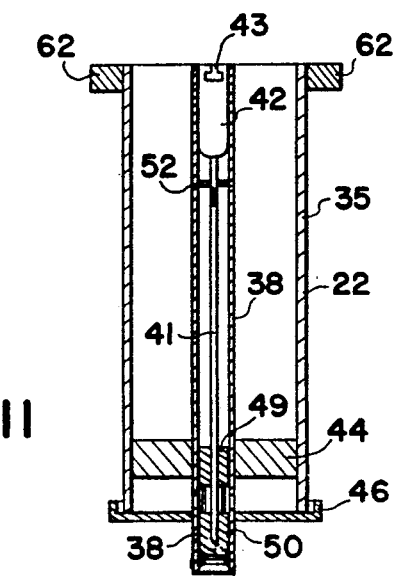
FIG 9
FIG 10
FIG 11

MEDICAL SYRINGE

BACKGROUND OF THE INVENTION

Much attention has been given in recent years to the danger of transmitting diseases by being pricked by used syringe needles. Many patents have issued on syringes having disposable protected needles, e.g., U.S. Pat. Nos. 4,927,414; 4,941,883; and 4,943,282.

There also have been some developments in providing a syringe which receives a capsule of the injection fluid, rather than to resort to puncturing the diaphragm of a supply bottle and sucking the injection fluid into the syringe before injecting it into the one being treated. Such an arrangement is shown in U.S. Pat. Nos. 2,193,322; 2,244,969; 2,705,956; and 3,583,399.

Combinations of these two features in a syringe have appeared in U.S. Pat. Nos. 4,808,169 and 4,834,717. There are, however, some complexities of these patented syringes that have been avoided in the present invention.

It is an object of the present invention to provide an improved medical syringe assembly that includes a cartridge of injectable fluid and a safety needle cover. It is another object of the present invention to provide an improved syringe assembly with a built-in cartridge of injection fluid and a sheathed needle which can be protracted for use and retracted for disposal with virtually no danger of injury to the user. Still other objects will become apparent from the more detailed description which follows.

BRIEF SUMMARY OF THE INVENTION

This invention relates to a syringe comprising a barrel assembly and a needle shield having a common vertical axis assembly; the barrel assembly including a hollow tubular barrel having a close top, an open bottom, and a plunger movable axially lengthwise inside the barrel by movement of a finger ring rigidly connected to the plunger by at least one connecting rod; the barrel including a central immovable locking rod rigidly attached to the top and extending to a free end about midway between the top and the bottom and having on the free end a locking button; the needle shield having a hollow cylindrical tubular body having a top, a bottom and a central axial tubular guide extending therethrough enclosing a tubular space for holding a liquid to be injected by the syringe, the axial tubular guide being open at both ends and containing slidably therein a hollow needle depending from a solid plug fitted with a locking slot to engage the locking button and to be locked thereto by a radial turning movement; the top of the shield being closed by an axially slidable, toroidal piston adapted to be contacted by the plunger and the bottom of the shield being closed by a fixed immovable cap; the axial guide having a first lateral passageway therethrough adjacent the bottom of the shield and the needle having a second lateral passageway therethrough capable of being aligned with the first lateral passageway when the plug and needle are positioned with the needle protracted from the guide at the bottom of the shield.

In preferred embodiments of the invention the needle has two spaced gaskets positioned respectively above and below a passageway through the needle wall which can be manipulated into position in alignment with a passageway through the axial tubular guide so as to permit injection fluid to flow from its confined reservoir in the needle shield to the hollow of the needle for injection purposes.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of the syringe barrel assembly of this invention;

FIG. 2 is a top plan view of the syringe barrel assembly of this invention;

FIG. 3 is a bottom plan view of the syringe barrel assembly of this invention;

FIG. 4 is a cross-sectional view taken at 4—4 of FIG. 2;

FIG. 5 is an exploded perspective view of the top of the syringe barrel assembly with the finger ring and connecting rods removed;

FIG. 9 is a front elevational view showing the needle shield inserted into the barrel assembly at the first station where the two components are locked together;

FIG. 10 is a front elevational view, partly in cross-section, showing the needle shield fully inserted at the third station where the syringe is ready to be used for an injection;

FIG. 11 is a front elevation, partly in cross-section, showing the needle shield after retraction of the needle and separation of the needle shield from the barrel assembly, ready for disposal.

DETAILED DESCRIPTION OF THE INVENTION

Figure 14:
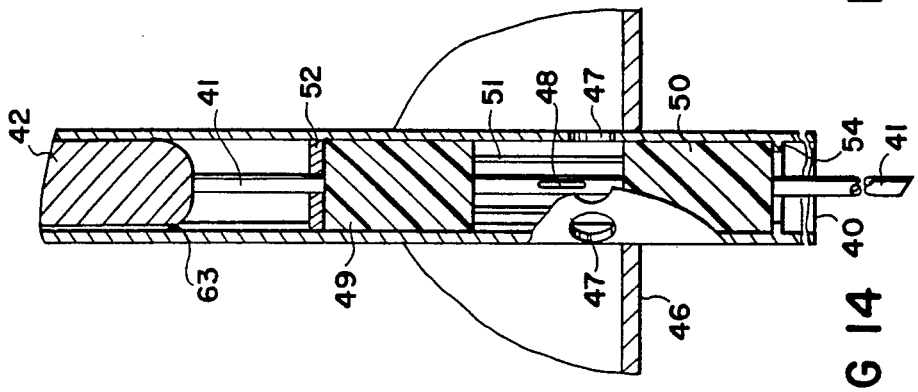
Figure 13:
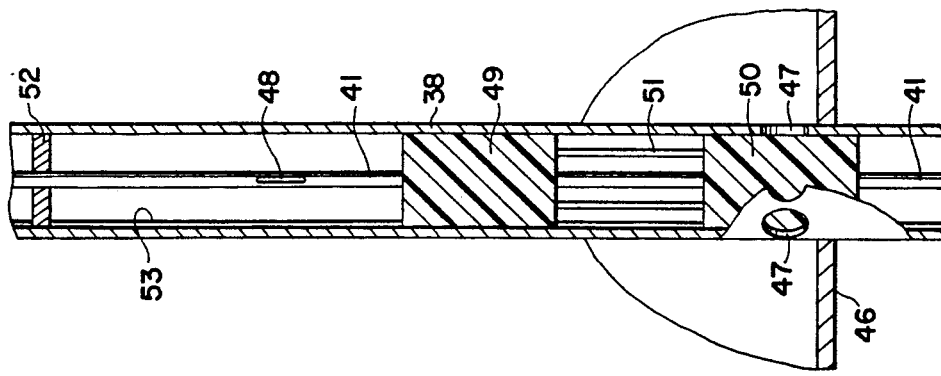
Figure 12:
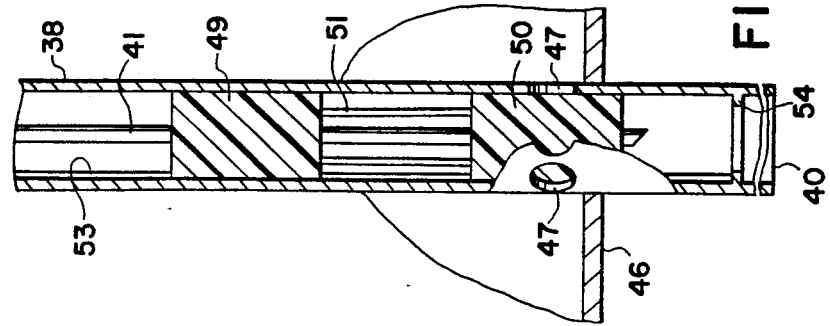

This invention is best understood by reference to the accompanying drawings. The assembly of the syringe is shown in FIGS. 8-11 which generally comprises a barrel assembly shown in FIGS. 1-5 and a needle shield assembly in FIGS. 6-7. The manner in which the needle is moved from a fully sheathed position to a fully operable protracted position is shown in FIGS. 12-14.

With particular attention to FIGS. 1-5 the barrel assembly 20 includes a thin tubular, preferably cylindrical, barrel body 22 with a top 23 closed by a cap 32 by way of cooperating screw threads 33 on the outside of body 22 and the inside of cap 32. Barrel body 22 has an open bottom 24. A plunger plate 25 inside of barrel body 22 is rigidly connected to a finger ring 27 by a plurality, preferably three, of connecting rods 28. Preferably, the connection between finger ring 27 and connecting rods 28 is by way of a base plate 72 welded to ring 27 and a threaded connection between each connecting rod 28 and base plate 72, i.e., threads on rods 28 to engage threaded bores in plate 72, or, alternatively to pass through unthreaded bores in plate 72 and be mated with nuts above plate 72. It is, of course, feasible to weld rods 28 to plate 72. In any event, rods 28 must be rigidly connected to plate 72 so as to be parallel to the central vertical axis 26 of the barrel assembly 20. The lower ends of rods 28 are rigidly connected to plunger plate 25 so that vertical movement of finger ring 27 produces a similar vertical movement in plunger 25. The connection between rods 28 and plunger plate 25 may be by threaded means, welding, or the like. On the lower surface of plate 25 are a plurality of pointed contacts 73 which will engage a soft piston in needle shield 21 so as to move the piston vertically. Finger ring 27 may be referred to as thumb ring 27 since the normal use of the syringe involves the thumb in ring 27. Also included in barrel assembly 20 is a finger grip locking rod unit 68 which includes two finger grips 34, to provide a location for fingers to cooperate with the thumb in moving plunger 25, and a locking rod 29. A preferred arrangement for finger grips 34 and locking rod 29 is a single unitary structure (shown in FIG. 5) that includes finger grips 34, ring 71, three equally spaced spokes 69, and locking rod 28 depending downwardly from the intersection of spokes 69. It is not critical, but merely convenient that this unitary structure be used for the finger grip locking rod component 68, since the finger grips 34 may be separate from locking rod 29. It is, however, necessary and critical that locking rod 29 be positioned accurately along the axis 26 of barrel body 22 so as to be properly positioned for easy coupling to needle shield assembly 21, which is described with reference to FIGS. 6 and 7. At the lower or free end 31 of locking rod 29 is a locking button 30 fashioned to fit into a mating slot in needle shield 21 so as to lock barrel assembly 20 to needle shield assembly 21 to provide a complete and operable syringe. Finger grip locking rod unit 68 preferably is clamped in place by the action of screwing cap 32 onto barrel body 22. A clamping ledge 56 is located around barrel body 22 as a rest for unit 68, preferably for reinforcing ring 71 if such a component is present. In order for these pieces to fit together, vertical slots 70 are cut in the top portion of barrel body 22 through the external threads 33 on barrel body 22, and spokes 69 extend slightly outward radially beyond barrel body 22 so as to rest in slots 70.

In order for barrel assembly 20 to be assembled from its various component parts cap 32 must have passageways 55 through its horizontal wall. These passageways 55 are large enough for connecting rods 28 to pass through.

As shown on FIG. 1, barrel body 22 has two diametrically opposed slot guides 57 which preferably are cut out portions in the walls of barrel body 22. Slot guide 57 is open at entrance 61 to receive tabs 62 of the needle shield 21 and guide needle shield 21 to a selected location. Slot guide 57 proceeds from entrance 61 vertically upward to about midway of the vertical length of barrel body 22. Slot guide 57 then takes a sharp turn to the right to first station 58, where locking button 30 is locked to locking slot 43 (see FIGS. 6-7). Slot 57 then proceeds vertically upward to two side branch locations 59 and 60 which are final locked positions for the syringe when ready to provide injections. Second station 59 is used when the needle is short or does not protract very much. Third station 60 is used for a longer needle or for one which is protracted a greater distance.

In any event, slot guide 57 is employed to connect barrel assembly 20 to needle shield 21 in any of three positions, 58, 59 or 60.

Figure 6:
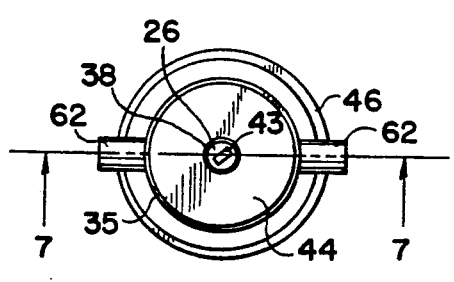
FIG. 6 is a top plan view of the needle shield assembly of this invention.
Figure 7:
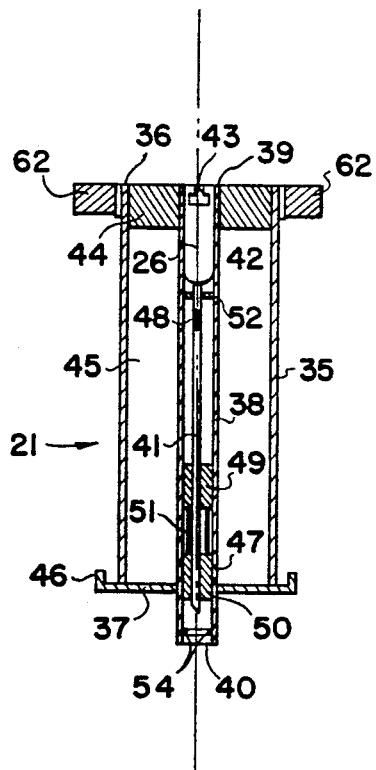
FIG. 7 is a cross-sectional view taken at 7—7 of FIG. 6.

In FIGS. 6 and 7 there is shown the needle shield 21. Needle shield 21 has a thin tubular body 35 and a central axial tubular guide concentric with body 35 about syringe axis 26. Piston 44 at the top end 39 and cap 46 near bottom end 40 enclose space 45 which is a reservoir for the injection fluid. Cap 46 is rigidly attached to body 35 as by welding. Piston 44 is a toroidal shape movable in a vertical direction outside of guide 38 and inside of body 35. The moving force for piston 44 is received from plunger 25, and the contact between plunger 35 and piston 44 is preferably made by barbed points 73 which can be pushed into rubbery piston 44, to provide a positive connection so that piston 44 can be moved up and down. Central tubular guide 38 is a small tube open at top and bottom ends 39 and 40. Vertically slidable inside tubular guide 38 are needle 41, needle plug 42, gaskets 49 and 50, spacers 51 and pusher washer 52. Needle plug 42 has a locking slot 43 in its upper surface adapted to receive locking button 30 of the barrel assembly 20 and upon a radial turning motion of needle plug 42 slot 43 becomes locked onto button 30. Needle plug 42 is formed with an external vertical spline or key 63 engaged with a corresponding vertical groove 53 in tubular guide 38 which prevents relative rotational motion between needle plug 42 and tubular guide 38. These features may be seen in FIGS. 11-14. Needle plug 42 serves as a base supporting hub for hollow needle 41 depending downwardly from plug 42. The overall length of tubular guide 38 is such that when needle plug is flush with top end 39, the needle 41 is completely sheathed and does not extend beyond bottom end 40. Tabs 62 extend radially outward in diametrically opposite positions from body 35 at its top end 39, and are of a size to slide easily along slot guide 57 in barrel body 20.

A short distance below needle plug 42 is a pusher washer 52 affixed rigidly to needle 41 and vertically slidable within tubular guide 38. A short distance below pusher washer 52 is a passageway 48 through the wall of needle 41 to communicate the hollow of needle 41 with the environment outside of needle 41. Farther down tubular guide are upper gasket 49 and lower gasket 50 spaced apart from each other and maintained in that spaced relationship by spacers 51 affixed at each end to gasket 49 and to gasket 50, respectively. Spacers 51 are a plurality of spaced rods or a screen mesh. Spacers 51 must be sufficiently rigid and strong to combine with gaskets 49 and 50 to make a unit that slides lengthwise inside tubular guide 38 and always maintains that same spaced relationship. In addition spacers 51 must not provide any serious obstruction to fluid flow in the space between gasket 49 and gasket 50. Tubular guide has at least one passageway 47 through its wall adjacent cap 46 which will permit injection fluid in space 45 to flow through passageway 47 into the space between gasket 49 and gasket 50 and through passageway 48 to the hollow of needle 41 and thence out its tip. Tubular guide 38 also includes an inwardly projecting flange 54 adjacent bottom end 40 to serve as a stop member to prevent gasket 50 from exiting out of guide 38.

Figure 8:
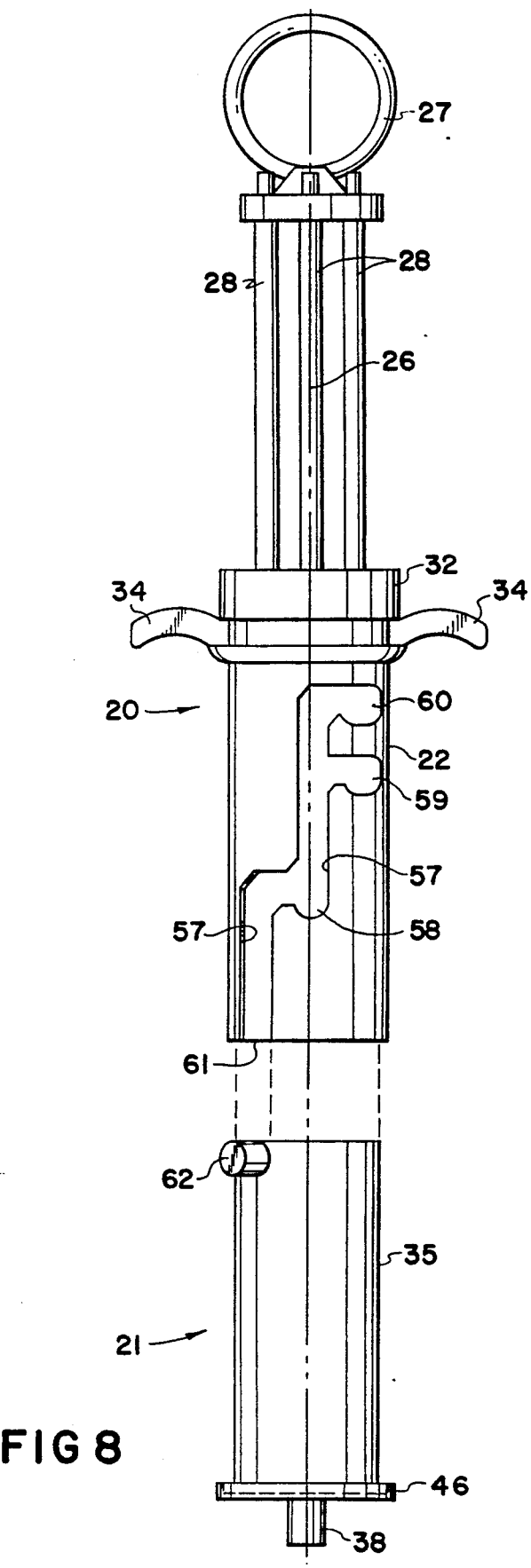
FIG. 8 is an exploded front elevational view of the syringe of this invention showing how the needle shield is attached to the barrel assembly
Figure 15:
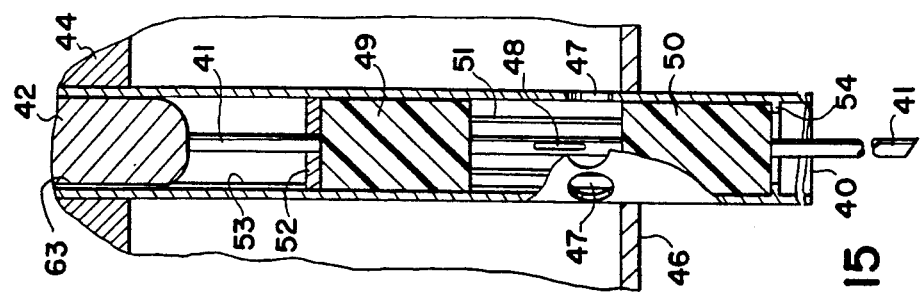
FIGS. 12-15 show enlarged vertical cross-sectional views of the needle and the tubular guide at different stages of progression from the time when the needle shield is attached to the barrel assembly to the time of injecting the fluid.

In FIGS. 8-15 the manner in which the syringe of this invention is illustrated. In FIG. 8 needle shield assembly 21 is aligned below barrel assembly 20 with tabs 62 ready to enter entrance 61 of slot guide 57. In FIG. 9 needle shield assembly 21 has been pushed upwardly into barrel assembly 20 until tabs 62 reach position 64 in slot guide 57. At this point locking button 30 of locking rod 29 has contacted locking slot 43 at the top surface of needle plug 42 of needle shield assembly 21. By turning needle shield assembly 21 clockwise until tabs 62 are in position 65 locking button 30 is locked into locking slot 43. This is the first station for the travel of tab 62 along slot guide 57. At this point needle shield assembly 21 is locked to barrel assembly 20, but needle 41 is still completely sheathed in tubular guide 38.

Needle shield assembly 21 is then pushed farther into barrel assembly 20 until tab 62 is in second station 59 or third station 60 (as shown in FIG. 10), which movement protracts needle 41 from lower end 40 of tubular guide 38. Since locking rod 29 is a fixed rigid rod, the movement upward of needle shield body 35 causes needle plug 42, needle 41, and pusher washer 52 to slide downward inside of tubular guide 38. These relationships are best seen in FIGS. 10–15. In FIG. 12 the positions of the components in tubular guide 38 are those when barrel assembly 20 and needle shield assembly are at the first station 58 as shown in FIG. 9, when needle 41 remains in its sheathed position. When needle shield assembly is pushed into barrel assembly beyond first station 58 on its way to second station 59 or third station 60, the components of needle shield assembly 21 are in positions as seen in FIG. 13. Needle 41 has been pushed downward, gaskets 49 and 50 remain as before. When tab 62 reaches third station 60 the needle shield components are positioned as shown in FIG. 14 and also in FIG. 10. Pusher washer 52 has contacted upper gasket 49 and pushed it downwardly along with spacers 51 and lower gasket 50 until lower gasket 50 is against stop flange 54 preventing any further movement in that direction. This leaves needle 41 in its greatest extension out of bottom 40 of tubular guide 38 ready to be used to inject fluid from space 45 into the target area. In the position of FIG. 13 passageways 47 are aligned with passageway 48 so as to permit free flow of fluid from reservoir space 45 to the hollow of needle 41. In FIG. 14 it is seen that piston 44 has been pushed downwardly to force fluid in space 45 through passageways 47 and 48 and out through needle 41.

After the injection of fluid needle 41 is withdrawn from the injected area and needle shield assembly is rotated to return tabs 62 to the vertical portion of slot guide 57 and pulled away from barrel assembly 20 as tabs 62 move downwardly in slot guide 57 and eventually barrel assembly 20 is separated from needle shield assembly 21. As shown in FIG. 11 needle 41 is again completely sheathed within lower gasket 50 to inhibit any fluid leakage therefrom. The needle 41 is thus completely inside of tubular guide 38 and safe for disposal. Barrel assembly 20 is available for reuse, preferably after sterilization. It is anticipated that there may be two different sizes of needle shield assemblies 21, differing only in the length of needle 41 for different types of injections. A shorter needle shield assembly can be used with second station 59 as the position for tab 62 when needle 41 is fully extended or protracted. Similarly third station 60 is used for a longer size needle 41 in a longer needle shield assembly 21.

Materials used in the syringe of this invention are those commonly used in other syringes. Barrel assembly 20 may be made of metal or plastic such that it can be sterilized without warping or destroying the structural integrity of the assembly, since this assembly can be used over and over again. Needle shield assembly is more likely to be made of plastic so as to be inexpensive enough to be used once and thrown away. Metal may be found in needle 41 and needle plug 42, but the remaining components can be made of plastic. Piston 44 should be a rubbery material sufficiently resilient to be pierced by contact barbed points 73 and to establish a good connection for transfer of force from plunger 25.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A syringe comprising a barrel assembly and a needle shield having a common vertical axis of assembly; said barrel assembly including a hollow tubular barrel having a closed top with at least one opening therethrough, an open bottom, and a plunger movable axially lengthwise inside said barrel by movement of a finger ring rigidly connected to said plunger by at least one connecting rod passing through said at least one opening of said top; said barrel including a central immovable locking rod rigidly attached to said top and extending to a free end about midway between said top and said bottom and having on said free end a locking button; said needle shield having a hollow cylindrical tubular body having a top, a bottom and a central axial tubular guide extending therethrough said tubular body and said axial tubular guide forming a tubular space therebetween for holding a liquid to be injected by the syringe, said axial tubular guide being open at both ends and containing slidably therein a hollow needle depending from a solid plug fitted with a locking slot to engage said locking button and to be locked thereto by a radial turning movement, said plug and needle being movable by axial movement of said needle shield toward said locking rod to dispose said locking button generally medially of said axial tubular guide when said needle is fully protracted; the top of said needle shield being closed by an axially slidable toroidal piston adapted to be contacted by said plunger and the bottom of said needle shield being closed by a fixed immovable cap; said axial tubular guide having a first lateral passageway therethrough adjacent the bottom of said shield and said needle having a second lateral passageway therethrough capable of being aligned with said first lateral passageway when said needle is moved by said locking rod to a position with said needle fully protracted from said axial tubular guide at said bottom of said needle shield.

2. The syringe of claim 1 wherein said needle includes a first gasket above said second lateral passageway and a second gasket below said second lateral passageway, with both said gaskets adapted to slide axially inside said guide and to maintain their spacing with respect to each other and with respect to said second lateral passageway.

3. The syringe of claim 2 wherein said axial tubular guide includes an inwardly extending flange adjacent said bottom of said shield adapted to stop said second gasket from axial movement beyond that point toward said bottom of said shield when said needle is fully protracted.

4. The syringe of claim 1 wherein said needle includes a washer rigidly affixed thereto adjacently below said plug in a lateral position and adapted to slide axially in said guide along with the axial movement of said needle and plug.

5. The syringe of claim 1 wherein said axial tubular guide includes a vertical groove parallel to said common vertical axis, and said plug includes a spline member engagable with said groove to prevent radial movement of said plug and needle in said needle shield.

6. The syringe of claim 1 wherein the axial length of said plug and said needle is less than the axial length of said axial tubular guide.

7. The syringe of claim 1 wherein said at least one connecting rod includes a pair of other connecting rods, said barrel assembly includes a tubular barrel with external screw threads around its outside adjacent said top, and a threaded cap with internal screw threads, said threaded cap having three spaced axial passageways therethrough to permit said three connecting rods to extend therethrough in an axial direction, a finger ring attached at upper ends of said connecting rods and connected to said plunger inside said threaded cap at lower ends of said connecting rods.

8. The syringe of claim 7 wherein said locking rod includes two laterally extending finger grip arms extending laterally outwardly from said tubular barrel at its top and clamped in place by the tightening of said threaded cap onto said tubular barrel by means of engagement of said external and internal screw threads.

9. The syringe of claim 1 wherein said barrel includes a pair of diametrically opposite grooved passageways extending from said bottom of said barrel to adjacent the top and said needle shield includes adjacent its said top a pair of diametrically opposed tabs extending laterally outward therefrom and adapted to engage said grooved passageways.

10. The syringe of claim 9 wherein said grooved passageway includes a first station wherein said locking button is engaged with said locking slot to connect said plug to said locking rod; a second station wherein said needle is protracted a short distance out of said guide; and a third station wherein said needle is protracted a long distance out of said guide.

11. A medical/dental syringe assembly comprising a barrel component, a locking rod finger grip component, and a shielded needle component which is attachable to and detachable from the barrel component to form a syringe having a common vertical axis; the barrel component including a threaded cap, a vertically movable connecting rod, and a thin tubular cylindrical body having an open bottom and an externally threaded open top closable by said threaded cap with vertical passageways therethrough to admit said vertically movable connecting rod having a thumb ring at its upper extremity and a plunger at its lower extremity inside said cylindrical body; said cylindrical body including two diametrically opposed vertical slot guides to direct said shielded needle component to a plurality of selected positions; said locking rod and finger grip component being generally T-shaped with the central locking rod positioned axially vertical inside said cylindrical body with a locking button at its lower extremity, and a pair of finger grip arms extending laterally outwardly from said cylindrical body; said locking rod and finger grip component being clamped in place by the force of said threaded cap being screwed down onto said arms and against a flange around the outside of said cylindrical body at the bottom of said external screw threads; said shielded needle component being a hollow cylindrical capsule having an upper end, a lower end, a central axial tubular guide containing an axially movable hollow needle and an enclosed tubular reservoir around said axial tubular guide to contain an injectable fluid, said needle being affixed to a solid plug slidable axially in said guide having a locking slot on its upper surface to engage said locking button and having a spline means to prevent radial movement, said capsule being movable axially after engagement between said locking button and said locking slot toward said locking rod to dispose said locking button generally medially of said capsule whereby said needle is slidingly disposed in its fully protracted position, said capsule including an axially movable piston at its upper end which is adapted to be engaged by said plunger, and two diametrically outwardly projecting tabs to engage said slot guides, said axial tubular guide having a first lateral passageway adjacent said lower end to allow fluid flow from said reservoir to the inside of said axial tubular guide; and said needle having a second lateral passageway therethrough to allow fluid flow from said tubular guide into the hollow of said needle, said needle including a pair of spaced gaskets on opposite ends of said second lateral passageway to prevent fluid leakage past said gaskets, a pusher plate affixed to said needle between said plug and the nearest adjacent said gasket, and a stop flange on the internal portion of said axial tubular guide adjacent its lower end to prevent said gaskets from moving out of said axial tubular guide.

12. The syringe of claim 11 wherein said gaskets are affixed to each other by spacer elements attached to both gaskets.

13. The syringe of claim 11 wherein said locking rod finger grip component is a single rigid member comprising a horizontal ring with three equally spaced spokes extending from said ring to a central axial locking rod depending downwardly from said spokes, and two diametrically opposed curved finger grip arms extending outwardly from said ring, said ring being adapted to closely fit over the outside of said barrel body and rest on said flange.

14. The syringe of claim 11 wherein said slot guides include a first station wherein radial movement between said barrel body and said cylindrical capsule causes said locking button to mate with said locking slot and join said locking rod to said plug; a second station wherein said needle is protracted a short distance outside of said bottom of said tubular guide; and a third station where said needle is protracted a long distance outside of said bottom of said tubular guide.

15. A reuseable syringe comprising a barrel assembly and a needle shield assembly having a common vertical axis, said barrel assembly including a hollow tubular barrel having a closed top, an open bottom, and an elongated plunger extending through an opening in said closed top and movable axially lengthwise inside said barrel by movement of a thumb ring rigidly connected to said plunger by at least one connecting rod, said barrel assembly including a central immovable elongated locking rod having a free end and an upper end rigidly attached to said top, said free end including a locking button, said needle shield assembly including a hollow cylindrical tubular body having an upper end and lower cover and a central axial tubular guide extending between said covers and enclosing a tubular space for holding a liquid to be injected by said syringe, said axial tubular guide being exposed and open at each end and containing therein a slidable hollow needle depending from a slidable solid plug which is fitted with a locking slot to engage said locking button and to be locked thereto by a radial turning movement, said needle being fully protracted by axial movement of said needle shield toward said locking button to dispose same generally medially of said needle guide, said upper end of said shield assembly being closed by an axially slidable toroidal piston adapted to be contacted by said plunger and said bottom of said shield assembly being closed by a fixed immovable cap, said axial tubular guide having a first lateral passageway therethrough above and adjacent said cap, said needle having a second lateral passageway therethrough capable of being in fluid communication with said first lateral passageway when said plug and said needle are positioned with needle protracted from said guide beyond said cap, said needle being retracted within said guide automatically by removal of said shield assembly from said syringe after removal of said plunger from said needle shield assembly.

16. The syringe of claim 15 wherein said needle includes a first seal above said second lateral passageway and a second seal below said second lateral passageway, with both said seals being adapted to slide axially within said guide and to maintain their spacing with respect to each other and with respect to said second lateral passageway.

17. The syringe of claim 16 wherein said axial tubular guide includes an inwardly extending flange adjacent said lower cover to stop said second seal from further axial movement to accurately locate said second passageway with said needle protracted.

18. The syringe of claim 15 wherein said needle includes a washer rigidly affixed thereto adjacently below said plug in a lateral position and adapted to slide axially in said guide together with said needle and plug.

19. The syringe of claim 15 wherein said axial tubular guide includes a vertical groove parallel to said axis, said plug including a spline member engaged with said groove to inhibit radial movement of said plug and said needle in said shield assembly.

20. The syringe of claim 15 wherein said plug and said needle combined axial length is less than an axial length of said axial tubular guide.

21. The syringe of claim 15 further comprising two additional connecting rods, said barrel assembly including a tubular barrel having external screw threads around its outside adjacent said top, said barrel assembly further including a threaded cap with internal screw threads, said cap having three spaced passageways therethrough to permit three equally spaced said connecting rods to move therethrough in an axial direction, said thumb ring being connected to each said plunger at its upper end and inside said cap at its lower end.

22. The syringe of claim 21 wherein said locking rod includes a pair of laterally extending finger grips extending laterally outwardly from said tubular barrel adjacent its top and clamped in place by tightening said threaded cap internal threads onto said tubular barrel external threads.

23. The syringe of claim 15 wherein said barrel component includes a pair of diametrically opposite grooved passageways extending from the bottom of said barrel to adjacent said top, said needle shield including adjacent its upper cover a pair of diametrically opposed tabs extending laterally outward therefrom and adapted to slidingly engage respective said grooved passageways.

24. The syringe of claim 23 wherein each said grooved passageway includes a first station wherein said locking button is engaged with said locking slot to connect said plug to said locking rod, a second station wherein said needle is protracted a short distance outwardly from said guide, and a third station wherein said needle is protracted a long distance out of said guide whereby two differing length needles in differing needle shield assemblies may be used in said syringe.

25. A reuseable syringe assembly comprising a barrel, a locking rod, a thumb ring, a shielded needle which is attachable to and detachable from said barrel, said barrel including a thin tubular cylindrical body having an outside wall, an open bottom and an externally threaded open top enclosable by a threaded cap with vertical passageways therethrough to admit a vertically movable connecting rod attached to said thumb ring at its upper extremity and a plunger at its lower extremity inside said cylindrical body, said body including two diametrically opposed vertical slot guides to direct said shielded needle to a plurality of selected positions, said locking rod being generally T-shaped with a central locking rod positioned axially vertically inside said body, said locking rod having a locking button at its lower extremity, a pair of finger grip arms extending laterally outwardly of said body, said locking rod being clamped by a force of said threaded cap being screwed down onto said arms and against a flange around said outside of said cylindrical body located adjacent the lower termination of said external screw threads, said shielded needle being formed of a hollow cylindrical capsule having an upper end, a lower end, a central axial tubular guide containing an axially movable hollow needle and an enclosed tubular medicinal reservoir around said axial tubular guide to contain an injectable fluid, said needle being affixed to a solid plug slidable axially in said guide and having a locking slot on its upper surface to engage said locking button and having a spline means between said guide and said plug to prevent radial movement, said capsule including an axially movable piston at its upper end which is adapted to be engaged by said plunger, and two diametrically outwardly projecting tabs to engage said slot guides, said axial tubular guide having a first lateral passageway adjacent said lower end to allow fluid flow from said reservoir inwardly into said tubular guide, said needle having a second elongated and lateral passageway therethrough to allow fluid flow from said tubular guide into said hollow of said needle, said needle including a pair of spaced seals located on opposite ends of said second passageway to inhibit fluid leakage, a pusher plate affixed to said needle adjacently below said plug adapted to engage an adjacent said seal when said needle and plug are moved downwardly in said axial tubular guide, a stop flange connected to said axial tubular guide adjacent its lower end to prevent adjacent said seal from exiting from said axial tubular guide and to accurately position said second passageway of said needle said needle being movable from a fully retracted position to a fully protracted position by axial movement of capsule toward said locking rod after engagement of said locking slot of said plug with said locking button to dispose said locking button generally medially of said axial tubular guide.

26. The syringe of claim 25 wherein said seals are affixed to each other by spacer elements attached to each said seal to maintain a seal spaced for fluid to flow between said passageways.

27. The syringe of claim 25 wherein said slot guides include a first station wherein radial movement between said barrel body and said cylindrical capsule causes said locking button to mate with said locking slot and join said locking rod to said plug, a second station wherein said needle is protracted a short distance outwardly from the bottom of said tubular guide, and a third station where said needle is protracted a long distance outside of the bottom of said tubular guide whereby two differing length needles in different capsules may be used in said syringe with their respective needle second passageway located substantially the same in fluid communication with said first passageway.

28. The syringe of claim 25 wherein said finger grip component includes a horizontal ring with three equally spaced spokes extending from said horizontal ring and intersecting centrally therein and carrying said locking rod depending downwardly therefrom, said thumb ring further including a horizontal member attached to said connecting rod, said horizontal member being adapted to closely fit inside of said barrel and push against said piston of said capsule.

29. The syringe of claim 28 wherein said horizontal member includes a plurality of spaced barbs to engage said piston and to cause movement of said piston in either downward or upward movement of said thumb ring, and said horizontal member.

30. The syringe of claim 25 wherein said seals after being moved into their positions by said pusher plate with said needle in its fully protracted position remain in their positions upon retraction of said needle into said guide by removal of said capsule from said barrel.

* * * * *